July 8, 1958 R. SCHREINER Plant Pat. 1,728
IRIS PLANT
Filed June 7, 1957
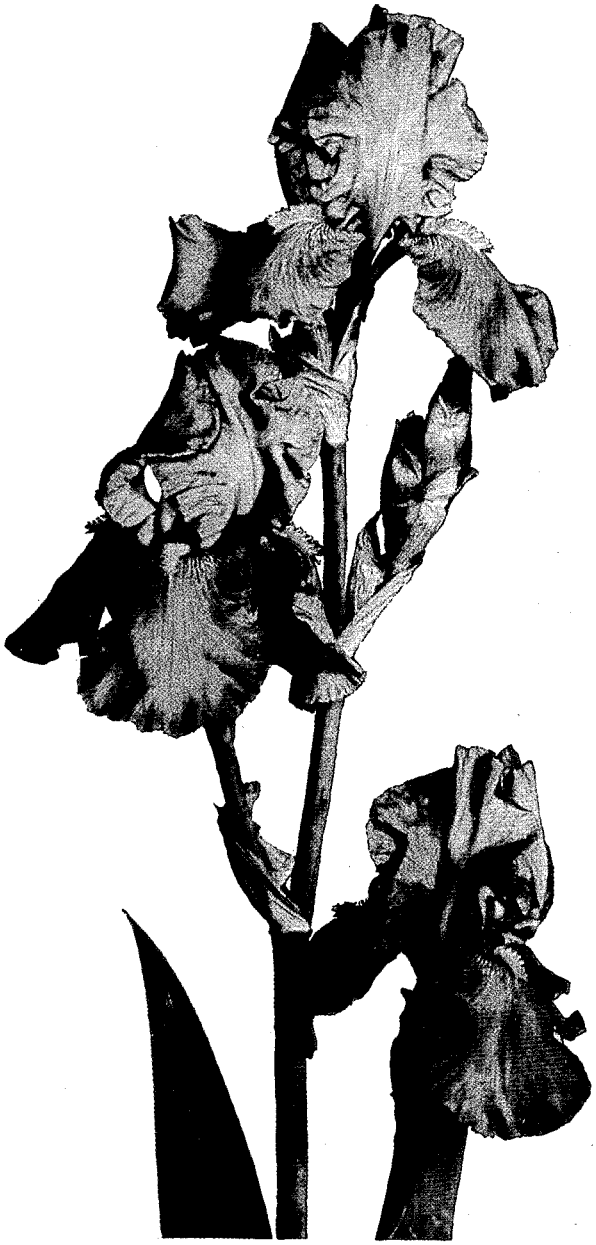
INVENTOR:
ROBERT SCHREINER
BY Rummler and Snow
ATT'YS United States Patent Office Plant Pat. 1,728

Patented July 8, 1958

1,728

IRIS PLANT

Robert Schreiner, Salem, Oreg.

Application June 7, 1957, Serial No. 664,450

1 Claim. (Cl. 47—60)

The present discovery relates to a new and distinct variety of iris plant, red-copper in color, which originated from a cross of the variety "Copper Medallion" (the seed parent) (unpatented) and "Inca Chief" (the pollen parent) (unpatented). The cross that produced this new variety was made by me in 1952 at my nursery in Salem, Oregon; and the first bloom of this new variety appeared in May of 1954.

My new variety of iris plant has been found to hold its distinguishing characteristics through succeeding generations by the division of rhizomes, as performed at Salem, Oregon. It propagates easily and at a good rate of reproduction.

This brilliant coppery-hued iris outshines all previous, known varieties of iris in its color class.

The primary object in carrying out this invention was to establish the distinctive Vinaceous-Rufous coloring of the flowers, in combination with the size and form of the blooms, and vigorous growth.

The accompanying illustration shows a stem of flowers and leaves in approximately true full colors.

In the following detailed description, color plate references indicate Ridgway's Color Standards and Nomenclature, while other colors refer to the ordinary dictionary meaning of the terms.

This new variety of iris is beautifully formed with well-cupped standards and moderately flaring falls. There is a pronounced ruffling or crimping of both the erect cluster of petals and the gracefully flaring lower petals. This ruffling extends from the outer margin of the petals inward for approximately fully one-half inch from the edge of the petals, and occasionally three-fourths of an inch.

The predominant color of this new bronze variety is Vinaceous-Rufous (Plate XIV). This uniform bronze general color tonality pervades throughout the entire bloom with the standards just a trifle lighter than the falls. The erect petals have a marked silken sheen, while the falls have a lustrous, velvety, golden nap, giving the bloom unusual brilliance. Barely discernible is an orange-yellow venation at the haft, extending to about ⅜ of an inch from the outer end of the beard, which is golden yellow and very uniform in coloring. There is an infusion of Ochraceous-Orange (Plate VX) at the base of the standards where the latter are attached to the stem, and the three style-arms in the center of the flower are also Ochraceous-Orange in color.

The texture of this new variety of iris is unusually heavy with excellent capacity to resist the buffeting of wind and rain. Unlike most other so-called "copper blends," this new variety has a remarkable ability to resist bleaching in hot sunshine, even when the thermometer is as high as 94° in the shade.

In size this variety of iris surpasses all other copper-toned iris, having blooms 6½ to 7 inches in height and 5½ to 6 inches in diameter. Each stem produces an average of nine blooms over a period of two to two and one-half weeks in the spring. It does not rebloom in the autumn in the climate of Salem, Oregon, where it is produced. It is an early mid-season bloomer.

A day or two before the buds of this new variety open, they are three inches in length and in color are between Vinaceous-Rufous and Hay's Russet (Plate XIV).

The filament of this new variety of iris which supports the anther is 1⅞ inches long. The filament bears an anther ¾ of an inch in length, and carries creamy-white pollen which is very fertile.

This new variety of iris plant reaches a height of 38 inches with two well-spaced candelabrum branches and one smaller branch at the bottom closer to the stem.

The stem is a medium deep green with the spathes a lighter green with a touch of bronze at the edge of the paper portion of the spathe.

The foliage of this new variety is vigorous and healthy but not distinguishable in color from the customary medium green shade of iris foliage. It is approximately 28 inches in height and 1½ to 2 inches in width. The foliage of this new variety is very resistant to leaf spot, which is the only iris foliage disease prevalent in Oregon. Trials of the new variety have been conducted in Salem, Marion County, Oregon, in extreme variable weather, some most apt to promote excessive leaf spot. The new variety has been carefully tested and observed for several years with respect to its growing habits and its resistance to leaf spot. The results of these trials and tests have demonstrated that the before mentioned qualities of the new variety are firmly fixed and that resistance to leaf spot is inherent in the new variety. The foliage retains its color from spring until late fall.

The foregoing features definitely differentiate my new variety of iris from its parents as well as from all other varieties of its class of which I am aware.

The two varieties of iris in commerce which more nearly approach my new variety in appearance are "Inca Chief" (unpatented) and "Pretty Quadroon" (unpatented).

The principal differences are as follows:

Compared to "Inca Chief," my new variety is less yellow-copper and more red-copper in tone; about six inches taller; more heavily ruffled; more graceful in form; slightly larger; and better branched.

Compared to "Pretty Quadroon," my new variety is less dusky or smoky; more vivid in its Vinaceous-Rufous color; four inches taller on the average; far more heavily ruffled (as "Pretty Quadroon" is only slightly ruffled); about 25% larger; and better branched.

The outstanding features of novelty and distinctiveness of my new variety are as follows:

Its uniform brilliant coppery tone.

Its resistance to wind, rain and hot sunshine.

Its well-cupped erect petals and graceful flaring lower petals.

Its pronounced ruffling on the outer edges of the petals.

Its size, number of blooms per stem produced over a period of a couple of weeks.

Its height and well-spaced branching.

Its vigorous growth and resistance to leaf spot.

Its retention of green coloring of the foliage from spring until late fall.

Its easy propagation and good reproduction.

Its very fertile pollen.

Having thus disclosed my invention, I claim:

A new and distinct variety of iris plant, substantially as herein shown and described, characterized particularly by its uniform Vinaceous-Rufous coloring of the flowers, its well-cupped erect petals and graceful flaring lower petals, pronounced ruffling of the outer edges of the petals, large size and number of blooms, the heavy texture of the blooms which resists wind, rain and hot sunshine, its height and well-spaced stem-branching, and its resistance to leaf spot.

No references cited.